(12) United States Patent
Andreasen et al.

(10) Patent No.: US 6,291,440 B1
(45) Date of Patent: Sep. 18, 2001

(54) IRON-DEXTRAN COMPOUND FOR USE AS A COMPONENT IN A THERAPEUTICAL COMPOSITION FOR PROPHYLAXIS OR TREATMENT OF IRON-DEFICIENCY

(75) Inventors: Hans Berg Andreasen, Viby Sjælland; Lars Christensen, Roskilde, both of (DK)

(73) Assignee: Pharmacosmos Holding A/S, Roskilde (DK)

( * ) Notice: Subject to any disclaimer, the term of this patent is extended or adjusted under 35 U.S.C. 154(b) by 0 days.

(21) Appl. No.: 09/509,454

(22) PCT Filed: Mar. 24, 1999

(86) PCT No.: PCT/DK99/00160

§ 371 Date: Mar. 29, 2000

§ 102(e) Date: Mar. 29, 2000

(87) PCT Pub. No.: WO99/48533

PCT Pub. Date: Sep. 30, 1999

(30) Foreign Application Priority Data

Mar. 25, 1998 (DK) ................................................ 420/98

(51) Int. Cl.[7] ........................ A61K 31/66; A61K 31/715; C07H 3/06; C08B 37/02

(52) U.S. Cl. ........................ 514/59; 514/112; 514/124; 536/112; 536/113; 536/114; 536/124

(58) Field of Search .............................. 536/113, 114, 536/112, 124; 514/59

(56) References Cited

U.S. PATENT DOCUMENTS

| Re. 24,642 | 4/1959 | London et al. ................ 167/68 |
|---|---|---|
| 2,885,393 | 5/1959 | Herb ............................ 260/209 |
| 3,093,545 | 6/1963 | Westfall et al. ................ 167/68 |
| 3,697,502 | 10/1972 | Christensen .................. 260/209 |
| 4,104,078 | 8/1978 | Barker et al. .................. 127/46 |
| 4,827,945 | 5/1989 | Groman et al. ................ 128/653 |
| 4,927,756 * | 5/1990 | Schwengers .................. 435/103 |
| 5,102,652 | 4/1992 | Groman et al. ................ 424/9 |

FOREIGN PATENT DOCUMENTS

| 117730 | 3/1960 | (DK) . |
|---|---|---|
| 129942 | 10/1967 | (DK) . |
| 129353 | 3/1968 | (DK) . |
| 122398 | 7/1968 | (DK) . |
| 1040467 | 8/1966 | (GB) . |
| 1076219 | 9/1967 | (GB) . |
| 1200902 | 8/1970 | (GB) . |

OTHER PUBLICATIONS

Dumitriu, S. (ed.). Polysaccharides in Medicinal Applications (Chapter 16 Medical Applications of Dextran and Its Derivatives by Anthony De Belder), Marcel Dekker, Inc., pp. 511, 512 & 520, 1996.*

Database WPI AN– 98–310208, Abstract, 1997.

Spectroscopy Letters, 28(2), 167–176(1995) "Structure Study""Dextrane" by Calsie, et al.

* cited by examiner

*Primary Examiner*—Kathleen Kohler Fonda
*Assistant Examiner*—Leigh C. Maier
(74) *Attorney, Agent, or Firm*—Sughrue, Mion, Zinn, Macpeak & Seas, PLLC

(57) ABSTRACT

An iron-dextran compound for parenteral treatment of iron-deficiency anemia comprises hydrogenated dextran having a weight average molecular weight (Mw) between 700 and 1,400 Daltons, preferably approximately 1,000 Daltons, a number average molecular weight (Mn) of 400 to 1,400 Daltons and wherein 90% by weight of the dextran has molecular weights less than 2,700 Daltons and the Mw of the 10% by weight fraction of the dextran having the highest molecular weights is below 3,200 Daltons, said hydrogenated dextran having been subjected to purification by membrane processes having a cut-off value between 340 and 800 Daltons, in stable association with ferric oxyhydroxide. The compound is produced by using membrane processes to eliminate dextrans of higher molecular weights than approximately 2,700 Daltons and membrane processes to remove saccharides of molecular weights below approximately 340 Daltons from hydrogenated dextran before precipitating ferric hydroxide in the presence of said dextran followed by heat treatment and purification.

18 Claims, No Drawings

IRON-DEXTRAN COMPOUND FOR USE AS A COMPONENT IN A THERAPEUTICAL COMPOSITION FOR PROPHYLAXIS OR TREATMENT OF IRON-DEFICIENCY

This a U.S. National stage application of PCT/DK99/00160, filed Mar. 24, 1999.

BACKGROUND OF THE INVENTION AND PRIOR ART

Iron-deficiency anemia has been described as one of the most common—possibly the most common—pathological conditions among humans when viewed on a global basis. Also in modern farm-breeding of pigs and other domestic animals iron-deficiency anemia is a problem unless suitable prophylactic measures are taken.

Although iron-deficiency anemia can often be prevented or cured by oral administration of iron-containing preparations, it is in many cases preferred to use parenterally administrable iron preparations to avoid variations in bio-availability of oral administrations and to ensure effective administration.

Therefore, iron-containing preparations for parenteral use, that means subcutaneous, intramuscular or intravenous administration, have for many years been at the disposal of the veterinary or human medical practitioner.

Although various iron-containing substances have been used or suggested as components in parenterally injectable preparations against iron-deficiency anemia, the most common preparations accepted today are such which comprise a combined product of ferric oxyhydroxide (or ferric hydroxide) in association with dextran. Dextran is a polymeric carbohydrate produced by the microorganisms Leuconostoc mesenteroides.

An iron-containing preparation for parenteral injection should obviously satisfy several requirements including ready availability of the iron for haemoglobin synthesis, absence of local or general side-effects and stability on storage enabling a satisfactory shelf-life at ambient temperature.

Iron-dextran preparations for the treatment of anemia have been marketed for decades, and many variations in the manufacturing process and in the selection of starting materials have been suggested with a view to improving the stability of such preparations and to decrease the amount of side effects obtained at their administration.

As examples of patents dealing with these problems the following may be cited:

U.S. Pat. No. 2,885,393 (1959) describes a basical process of producing an iron-dextran complex in which the average molecular weight of the dextran is 30,000 to 80,000 Daltons or lower. The suitability of these complexes for human therapy does not appear from this patent specification.

U.S. Pat. No. Re. 24,642 (1959) comprises a detailed explanation of the requirements to an iron solution intended for intramuscular injection, incorporated herein by reference. The patent deals with a substantially nonionic complex of ferric hydroxide with a dextran having an average intrinsic viscosity at 25° C. of about 0.025 to about 0.25, as well as a process for preparing such a complex by contacting a dextran as described with ferric hydroxide formed in situ by reaction between a ferric salt and an alkali base. No information as to the desired molecular weight of the dextran is given, and no chemical modification of the dextran, apart from a partial depolymerisation, is suggested.

U.S. Pat. No. 3,093,545 (1963). This patent discloses some details such as temperatures and pH-values in an improved method of preparing a product apparently very similar to the one prepared in the last mentioned above patent.

GB 1,200,902 (1970) teaches that in contrast to preparing the ferric hydroxide in situ it is advantageous to preform the ferric hydroxide under controlled conditions since such ferric hydroxide will readily form complexes with dextrans. It is stated that not only partially depolymerised dextran having a weight average molecular weight in the range of for example 500–50,000 Daltons, preferably in the range 1,000–10,000 Daltons, but also modified forms or derivatives of dextran such as hydrogenated dextrans or oxidised dextrans or alkali treated dextrans come into consideration as theoretical possibilities. However, the only dextrans specifically mentioned are oxidized dextrans having an average molecular weight of 3,000 and 5,000 Daltons, resp. The ferric hydroxide is prepared before contact with the dextran. This means that the resulting product consists of ferric oxyhydroxide on which the dextran forms a coating in contrast to the more homogeneous products formed by precipitating the ferric hydroxide in situ, that means in the presence of the dextran.

DK 117,730 (1970) deals with a process in which hydrogenated dextran having a molecular weight between 2,000 and 10,000 Daltons is reacted with ferric hydroxide in aqueous medium. The average molecular weight of the dextran used in the embodiment examples is not indicated. However, the intrinsic viscosity is stated as approximately 0,05 which could correspond to an average molecular weight of approximately 5,000 Daltons.

DK 122,398 (1972) also discloses the use of hydrogenated dextran for preparing complex compounds with ferric hydroxide, and it is explained that a substantial lower toxicity is obtained than when non-hydrogenated dextran is used. The subject of the patent is a process in which moist ferric hydroxide is mixed with dry hydrogenated dextran, and after optional addition of citric acid or citrate the mixture is heated and purified.

U.S. Pat. No. 3,697,502 (1972) discloses a process for producing an iron-dextran preparation in which citric acid is added to the dextran and a simultaneous addition of alkali metal hydroxide solution and ferric chloride solution is made. The average molecular weight of the dextran is between 3,000 and 20,000 Daltons. The dextran used in the embodiment examples has a molecular weight of 7,000 and 10,000 Daltons, resp.

DK 129,353 (1974) is directed on an analogy process for producing a ferric hydroxide-dextran derivative at an average molecular weight of the dextran of at the most 50,000 Daltons, and the terminal groups of the polymer chains thereof have been modified to convert the terminal reducing anhydroglucose unit into a corresponding carboxylic acid group. Although the limits indicated for molecular weight of the dextran are very broad, viz. from 500 to 50,000 Daltons, preferably from 1,000 to 10,000 Daltons, the only exemplified dextran has an average molecular weight of 5,000 Daltons.

DK 129,942 (1974) has similarity to the above last mentioned DK patent and deals with the manufacture of ferric hydroxide complexes with dextran hepton acid or dextrine hepton acid. The hepton acids are prepared by hydrolyzing the corresponding cyanhydrids.

U.S. Pat. Nos. 4,827,945 (1989) and 5,102,652 (1992) both deal with superparamagnetic metal oxides such as iron oxides coated with or associated with polymeric materials such as dextran. The polymer is contacted with a mixture of the metal oxides in two different oxidation stages to produce a superparamagnetic combined product which is afterwards oxidized to transform all the metal oxide into the highest of said oxidation steps. The product is especially useful as contrast agent in magnetic resonance imaging in medical diagnosis. However, it is also mentioned that they can be used for treatment of iron-deficiency anemia. The molecular weight of the polymers, including carbohydrates such as dextran are preferably from 5,000 to 250,000 Daltons.

GB patent 1,076,219 describes the production of an iron preparation, wherein the ferric hydroxide is bound to a complexforming agent consisting of sorbitol, gluconic acid and a oligosaccharide in a certain proportion, where sorbitol is the dominating component. In one of the examples in the specification of the patent a hydrogenated dextran with an average molecular weight of about 1000 Daltons is used as oligosaccharide. From the process described for the production of this dextran it can be deduced that its contents of very low molecular weight components must be high. Even more important in connection with the present invention is, however, cf. the explanation below, that at the time of complexformation a high amount of hydrogenated monomer of dextran, i.e. sorbitol, is present.

In spite of the several attempts to improve iron-dextran preparations for treatment of anemia, as reflected in the above patents, the preparations prepared according to the state of the art have still some drawbacks.

This is a result of the fact that in some patients the preparations may cause delayed hypersensitivity, or severe anaphylactic side effects, resulting f.inst. in dyspnea, hypotension, shock and death. Also other toxic reactions might be observed.

Besides, several of the prior art preparations are not able to meet current requirements as to stability. Lacking stability may manifest itself as gelatination of the liquid or precipitation of iron hydroxide or oxyhydroxide.

SUMMARY OF THE INVENTION

Based on investigations, tests and practical experiences we have now realized that the above mentioned drawbacks are associated with the presence of insufficiently hydrolyzed relatively high molecular weight dextran, although in tiny amounts, in the dextran used as starting material, as well as with the presence of low molecular weight saccharides therein.

It is generally recognized that high molecular weight dextrans involve a greater risk for anaphylactic reactions than do low molecular weight dextrans. Actually, it is current practice to reduce the risk for anaphylactic reactions when infusing clinical dextrans by a pre-treatment of the patient by injection of low molecular weight dextran such as a dextran having a weight average molecular weight Mw of approximately 1,000 Daltons.

The manufacture of dextran usually involves acid hydrolysis of dextrans of higher molecular weight followed by isolation and purifying operations including precipitation of the dextran, e.g. from an aqueous solution by addition of e.g. an alcohol.

By such a precipitation not only the desired fractions of the dextran precipitate, but also any dextran of higher molecular weight will precipitate, for which reason the recovered dextran fraction often contains high molecular weight dextrans which have not been cleft in the preceding acid hydrolysis.

Since even very small concentrations of high molecular weight dextrans are able to cause unpredictable and often rather severe anaphylactic reactions, it is a feature of the present invention that the presence of such dextrans must be avoided by substituting or supplementing the conventional precipitation processes by membrane processes capable of very efficiently eliminating the presence of high molecular weight dextrans before the desired dextran fraction is contacted with the iron compounds.

However, we have experienced that the removal of higher molecular weight dextrans from the desired dextran fraction having a weight average molecular weight of e.g. 1,000 Daltons, does not ensure that the resulting iron- dextran will be non-toxic and stable. It has also been revealed that the presence of low molecular weight carbohydrates such as monosaccharides resulting from the hydrolysis process creates difficulties.

The presence of such saccharides has hitherto been regarded as being of only minor importance. However, when the dextran containing such saccharides is reacted with iron, by precipitating ferric hydroxide in a solution thereof, not only dextran-iron association compounds are formed, but also the saccharides combine with the iron to form complex or association compounds.

However, these saccharide based iron compounds are far less stable than the dextran-iron compounds, and in aqueous solution they give rise to a certain concentration of free ferric ions and of low molecular weight saccharides, such as glucose.

As it is well known, free ferric ions exert a toxic action when present in preparations for parenteral administration. Besides, it has turned out that not only ferric ions but also low molecular weight saccharides cause instability of an aqueous iron-dextran solution, because of precipitation and/ or gel-forming reactions possibly resulting in a complete solidification of the solution within days or months. Besides, the presence of low molecular weight saccharides seems to increase the parenteral toxicity of an iron-dextran solution, apparently because the saccharides interfere with the binding of the iron compounds to the dextran, thereby forming free or only weakly bound ferric ions.

Although the binding between the low molecular weight saccharides and the iron compounds, as it follows from the above, is rather weak, it is sufficient for impeding an efficient removal of the saccharides and the free iron compounds by the dialysis process to which it is customary to subject the iron-dextran solution as an after-treatment.

Therefore, it is a further important feature of the invention that the dextran fraction must be purified by membrane processes removing low molecular weight saccharides before it is used in the reaction where the iron-containing complex or association compounds are formed.

The present invention thus deals with iron-dextran compounds having an extremely low frequency of non-desired side effects and being satisfactory stable, also during sterilization and storage as aqueous solutions, which iron-dextran compound can be used as component in a therapeutical composition for prophylaxis or treatment of iron-deficiency in animal or human subjects by parenteral administration, the iron-dextran compound being characterized in that it comprises hydrogenated dextran having a weight average molecular weight (Mw) between 700 and 1,400 Daltons, preferably approximately 1,000 Daltons, a number average molecular weight (Mn) of 400 to 1,400 Daltons and wherein 90% by weight of the dextran has molecular weights less than 2,700 Daltons and the Mw of the 10% by weight fraction of the dextran having the highest molecular weights is below 3,200 Daltons, said hydrogenated dextran having been subjected to purification by membrane processes having a cut-off value between 340 and 800 Daltons, in stable association with ferric oxyhydroxide.

In connection with the present invention the "weight average molecular weight" and the "number average molecular weight" mean the respective average molecular weight at the time where the formation of complexes takes place, based on all dextran molecules from the monomer and upwards.

It is believed that the reason why dextrans of the above defined molecular weight distribution have not found commercial applicability in the manufacture of iron-dextran compounds is that sufficient attention has not been paid to the presence of low molecular weight saccharides for which reason toxicity and inferior stability have been experienced, and that sufficient attention has not been paid to the fact that the dextrans of weight average molecular weight around 1,000 Daltons are better tolerated by the human or animal organism than the higher molecular weight dextrans conventionally used in iron preparations.

When used for parenteral administration, the compound in question is dissolved or dispersed in an aqueous liquid, and it may be marketed as such, preferably having an iron content of 5–20% w/v. On the other hand the compound is sufficiently stable to be dried without deterioration in a conventional drying process such as spray-drying, for which reason the compound can also be marketed as sole or partial constituent of a dry powder. The iron content thereof will typically be 15–45% w/w.

In relatively low molecular weight dextrans as those coming into consideration according to the present invention the influence of the terminal groups (partially hydrogenated aldehyde groups) on the polymer chains is substantially more pronounced than in dextrans of higher molecular weight, since, on a weight basis, the number of functional terminal groups is higher. These functional terminal groups tend to increase instability by reactions involving $Fe^{3+}$ and low molecular weight saccharides. Therefore, the absence of $Fe^{3+}$ and low molecular weight saccharides is even more important than when higher molecular weight dextrans are dealt with.

The invention also comprises a process for producing an iron-dextran compound as described above, which process is characterized in the following steps:

The molecular weight of dextran is reduced by hydrolysis, and the dextran is hydrogenated to convert functional aldehyde terminal groups into alcohol groups; the hydrogenated dextran as an aqueous solution is combined with at least one water soluble ferric salt; base is added to the resulting solution to form ferric hydroxide, and the resulting mixture is heated to transform the ferric hydroxide into ferric oxyhydroxide as an association compound with the dextran, which process is characterized in, that after the hydrolysis but before being combined with the water soluble ferric salt, the dextran is purified by one or more membrane processes using a membrane having a cut-off value suitable for holding back dextran of molecular weight above 2,700 Daltons, possibly followed by further hydrolysis, and followed by one or more membrane processes using membranes with a cut-off between 340 and 800 Daltons.

A preferred embodiment of the process comprises the following:

preparing an aqueous solution comprising the purified hydrogenated dextran and at least one water-soluble ferric salt;

adjusting the pH of said aqueous solution to a value above 10 by addition of a base;

heating the mixture to a temperature above 100° C. until it turns to a black or dark brown colloidal solution which can be filtered through a 0.45 μm filter; and further purification and stabilization using filtration, heating and membrane processes and addition of one or more stabilizers, and optionally drying the solution to obtain the desired iron-dextran compound as a stable powder. Injection liquids may be produced by redissolving this powder, adjustment of pH, sterilizing by filtration and filling into ampoules or vials. Sterilization may also be accomplished by autoclaving the filled ampoules or vials.

Alternatively the drying operation is omitted, and an injection liquid is produced from the purified solution without intermediate drying thereof.

In a further preferred embodiment the hydrogenation of the dextran is performed by means of sodium borohydride in aqueous solution.

The stabilization suitably takes place by addition of a salt of an organic hydroxy acid, preferably a citrate.

The invention also comprises use of a compound consisting of or containing a hydrogenated dextran having a weight average molecular weight of 700–1,400 Daltons, preferably approximately 1,000 Daltons, a number average molecular weight (Mn) of 400 to 1,400 Daltons and wherein 90% by weight of the dextran has molecular weights less than 2,700 Daltons and the Mw of the 10% by weight fraction of the dextran having the highest molecular weights is below 3,200 Daltons, in stable association with ferric oxyhydroxide, said hydrogenated dextran having been subjected to purification by membrane processes having a cut-off value between 340 and 800 Daltons, for the preparation of a parenterally administrable therapeutical composition for prophylaxis or treatment of iron deficiency anemia in animal or human subjects.

The invention is further illustrated by means of the following non-limiting examples.

EXAMPLE 1

(i) Hydrolysis and Hydrogenation of Dextran 2,522 kg hydrolysed dextran collected as permeate from a membrane having a cut-off value <5,000 Daltons, is hydrolysed at pH 1.5 at a temperature of 95° C.

The hydrolysis is monitored chromatographically using gel permeation chromatography (GPC), and is terminated by cooling when the molecular weight of the material being hydrolysed is estimated to have achieved the desired value, i.e. a weight average molecular weight of 700–1,400 Daltons.

By the hydrolysis low molecular weight dextran is produced but also glucose is formed. After cooling and neutralization the amount of glucose and very low molecular weight oligomers is reduced by membrane processes having a cut-off value of 340–800 Daltons. After this process, the content of dextran is determined by optical rotation ($\alpha_D 20$ ~200) to be 1,976 kg, and the amount of reducing sugar is determined by use of Somogyi's reagent to be 36.8%.

The reducing capability is decreased by treatment with sodium borohydride. For the 1,976 kg dextran 57 kg sodium borohydride is added at basic pH.

After the sodium borohydride treatment, the reducing capability is determined to 1.5%.

Hereafter the solution is neutralized to pH <7.0, and subsequently de-ionized. The average molecular weights and the molecular weight distribution is determined chromatographically.

The chromatography also reveals that the above conditions, viz. that 90% by weight of the dextran has molecular weights less than 2,700 Daltons and that the weight average molecular weight (Mw) of the 10% by weight Fraction of the dextran having the highest molecular weights is below 3,200 Daltons, are fulfilled.

Mw is found to be 1,217 and Mn is 845 Daltons. The final amount of dextran after de-ionization is 1,320 kg—determined by optical rotation.

(ii) Synthesis of Iron-dextran 120 kg dextran, produced as above, is as an 18% solution mixed with 150 kg $FeCl_3$, $6H_2O$.

To the agitated mixture, 93 kg $Na_2CO_3$ as a saturated aqueous solution is added, and, thereafter, the pH is raised to 10.5 using 24 liters concentrated aqueous NaOH (27% w/v).

The mixture thus obtained is heated above 100° C. until it turns to a black, dark brown colloidal solution which can be filtered through a 0.45 $\mu$m filter and subsequently cooled. After cooling the solution is neutralized using 12 liters concentrated hydrochloric acid to obtain a pH of 5.80 and is purified using membrane processes until the chloride content in the solution is less than 0.68% calculated on basis of a solution containing 5% w/v iron.

If the chloride content of the solution is less than desired to obtain an isotonic solution, sodium choride is added and pH is finally adjusted to 5.6 and the solution is filtered through a 0.45 $\mu$m (or alternatively a 0.2 $\mu$m) membrane filter.

The solution is spray dried and the iron-dextran powder is ready for marketing or for further processing.

As alternative to spray drying, the solution can be used for direct production of injection liquids having an iron content of e.g. 5%, as described above.

When using the iron-dextran powder for producing injection or infusion liquids the powder is re-dissolved in an aqueous medium, the pH is checked, and, if necessary, adjusted, and the solution is filled into ampoules or vials after being sterilized by filtration. Alternatively, the sterilization can take place by autoclaving after filling into ampoules or vials.

EXAMPLE 2

(i) Hydrolysis and Hydrogenation of Dextran

This portion of the synthesis is performed as described under (i) in Example 1 above, apart from the fact that 54 kg sodium borohydride is used and the reducing capability is thereby decreased to 3.0%.

(ii) Synthesis of Iron-dextran 120 kg of the above mentioned dextran as an 18% solution is mixed with 300 kg $FeCl_3$, $6H_2O$.

To the agitated mixture is added 180 kg $Na_2CO_3$ as a saturated aqueous solution, and thereafter the pH of the mixture is raised to pH 11.5 using 38 liters concentrated aqueous NaOH (27% w/v)

The mixture thus obtained is heated above 100° C. until it turns to a black, dark brown colloidal solution and can be filtered through a 0.45 $\mu$m filter after which it is cooled. The cooled solution is neutralized, using 25 liters concentrated hydrochloric acid, to pH 5.60 and is purified using membrane processes until the chloride content is less than 1.1% calculated on basis of a solution containing 10% w/v iron.

Thereafter a hydroxy acid in the form of 6 kg citric acid is added, and pH is adjusted to a pH above 8.0 using NaOH, and the solution is stabilized by raising the temperature to above 100° C. for 60 minutes.

Subsequently, pH is adjusted by means of concentrated hydrochloric acid to pH 5.6. In case the chloride content of the solution is less than desired, it is adjusted by adding NaCl.

Thereafter, the solution is filtered through a 0.45 $\mu$m (or 0.2 $\mu$m) membrane filter.

The solution is spray dried and the iron-dextran powder is thus finished.

This powder is suitable for producing a liquid iron-dextran preparation containing approximately 10% w/v iron.

EXAMPLE 3

(i) Hydrolysis and Hydrogenation of Dextran

This portion of the synthesis is performed as in Example 2 above.

(ii) Synthesis of Iron-dextran 80 kg of the above dextran as an aqueous 10% solution is mixed with 400 kg $FeCl_3$, $6H_2O$.

To the agitated mixture 232 kg $Na_2CO_3$ is added as a saturated aqueous solution and thereafter the pH of the mixture is raised to 11.5 using 60 liters concentrated aqueous NaOH (27% w/v).

The above mentioned mixture is heated above 100° C. until it turns to a black, dark brown colloidal solution and can be filtered through a 0.45 $\mu$m filter after which it is cooled. The cold solution is neutralized using 15 liters concentrated hydrochloric acid to pH 5.60 and is purified using membrane processes until the chloride content is less than 1.8% calculated on basis of a solution containing 20% w/v iron.

Thereafter hydroxy acid, constituted of 8 kg citric acid, is added and pH is adjusted with NaOH to a value above 8.0, after which the solution is stabilized by raising the temperature to above 100° C. for 60 minutes.

Thereafter pH is adjusted with concentrated hydrochloric acid to 5.6. In case the chloride content of the solution is less than desired, the chloride content is adjusted by adding NaCl. The solution is filtered through a 0.45 $\mu$m (or 0.2 $\mu$m) membrane filter.

The solution is spray dried and the iron-dextran powder is finished. This powder is suitable for producing a liquid preparation containing 20% w/v iron.

In all three examples, the yield of iron-dextran powder is above 95%, calculated on basis of the iron used in the process.

What is claimed is:

1. A hydrogenated dextran having a weight average molecular weight (Mw) of 700–1,400 Daltons, and a number average molecular weight (Mn) of 400–1,400 Daltons, wherein 90% by weight of the dextran has a molecular weight of less than 2,700 Daltons and the remaining 10% by weight of the dextran having a molecular weight of 2,700 or greater has a Mw of less than 3,200, wherein said hydrogenated dextran has been purified by membrane filtration, wherein said membrane has a cut-off value of 340–800 Daltons.

2. The compound of claim 1, wherein said hydrogenated dextran has a Mw of about 1,000 Daltons.

3. An iron-dextran compound consisting of hydrogenated dextran in stable association with ferric oxyhydroxide, wherein said hydrogenated dextran has a weight average molecular weight (Mw) of 700–1,400 Daltons, and a number average molecular weight (Mn) of 400–1,400 Daltons, wherein 90% by weight of the dextran has a molecular weight of less than 2,700 Daltons and the remaining 10% by weight of the dextran having a molecular weight of 2,700 Daltons or greater has a Mw of less than 3,200 Daltons, wherein said hydrogenated dextran has been purified by membrane filtration, wherein said membrane has a cut-off value of 340–800 Daltons.

4. The compound of claim 3, wherein said hydrogenated dextran has a Mw of about 1,000 Daltons.

5. A therapeutic composition for prophylaxis or treatment of iron deficiency in an animal or human and suitable for parenteral administration consisting essentially of a pharmaceutically effective amount of the iron-dextran compound of claim 3, and a pharmaceutically acceptable carrier or diluent.

6. The therapeutic composition of claim 5, wherein said compound is in the form of a dry powder.

7. The therapeutic composition of claim 5, wherein said composition is in the form of a dry powder.

8. The therapeutic composition of claim 6, wherein said dry powder has an iron content of 15–45% w/w.

9. The therapeutic composition of claim 7, wherein said dry powder has an iron content of 15–45% w/w.

10. The therapeutic composition of claim 5, wherein said composition is in the form of an aqueous solution or dispersion having dissolved or dispersed therein, respectively said compound.

11. The therapeutic composition of claim 10, wherein the resulting solution or dispersion has an iron content of 5–20% w/v.

12. A process for preparing the iron-dextran compound of claim 3, comprising the steps of:
  (a) hydrolyzing dextran so as to reduce its molecular weight,
  (b) hydrogenating the resulting hydrolyzed dextran to convert functional aldehyde terminal groups into alcohol groups,
  (c) combining the resulting hydrogenated dextran, as an aqueous solution, with at least one water soluble ferric salt,
  (d) adding base to the resulting aqueous solution to form ferric hydroxide, and
  (e) heating the resulting basic solution to transform the ferric hydroxide into ferric oxyhydroxide in association with said dextran,
  wherein after said hydrolyzing, but prior to combining the resulting hydrogenated dextran with said water-soluble ferric salt, said dextran is purified using a membrane having a cut-off value above 2,700 Daltons, optionally followed by further hydrolysis, followed by purifying using a membrane having a cut-off value of 340–800 Daltons.

13. The process of claim 12, wherein in step (d), the resulting solution is adjusted to a pH above 10 using said base, and wherein in step (e), heating is carried out at a temperature above 100° C. until the solution turns into a black or dark brown colloidal solution, which is then filtered through a 0.45 $\mu$m membrane; and thereafter a stabilizer is added, and optionally the solution is dried to obtain a stable powder.

14. The process of claim 12, wherein said hydrogenating in step (b) is performed using sodium borohydride in aqueous solution.

15. The process of claim 13, wherein said stabilizer is at least one salt of an organic hydroxyacid.

16. The process of claim 15, wherein said organic hydroxyacid is a citrate.

17. A process for preparing the composition of claim 5, comprising dissolving or dispersing said compound in an aqueous liquid.

18. The process of claim 17, wherein the resulting solution is sterilized by filtration and thereafter the resulting sterilized liquid is placed in an ampoule or vial or, the resulting solution is placed in an ampoule or vial and thereafter, the resulting ampoule or vial containing said liquid is autoclaved.

* * * * *